US008642016B2

(12) United States Patent
Chau et al.

(10) Patent No.: US 8,642,016 B2
(45) Date of Patent: Feb. 4, 2014

(54) MEDICINAL DELIVERY SYSTEM, AND RELATED METHODS

(75) Inventors: Tommy L. Chau, Ashburn, VA (US); John M. Pinney, St. Michaels, MD (US); Jack E. Henningfield, Baltimore, MD (US); Edward J. Cone, Severna Park, MD (US); Saul M. Shiffman, Pittsburgh, PA (US); Joseph G. Gitchell, Chevy Chase, MD (US)

(73) Assignee: JSRNTI, LLC, Bethesda, MD (US)

( * ) Notice: Subject to any disclaimer, the term of this patent is extended or adjusted under 35 U.S.C. 154(b) by 901 days.

(21) Appl. No.: 11/878,163

(22) Filed: Jul. 20, 2007

(65) Prior Publication Data

US 2008/0020050 A1    Jan. 24, 2008

Related U.S. Application Data

(60) Provisional application No. 60/832,127, filed on Jul. 21, 2006.

(51) Int. Cl.
*A61K 9/68* (2006.01)
(52) U.S. Cl.
USPC .......................................................... 424/48
(58) Field of Classification Search
USPC .......................................................... 424/48
See application file for complete search history.

(56) References Cited

U.S. PATENT DOCUMENTS

| | | |
|---|---|---|
| 1,038,227 A | 9/1912 | Sulzberger |
| 2,262,087 A | 11/1941 | Bartlett |
| 2,536,168 A | 1/1951 | Goggin |
| 3,845,217 A | 10/1974 | Ferno et al. |
| 3,877,468 A | 4/1975 | Lichtneckert et al. |
| 3,901,248 A | 8/1975 | Lichtneckert et al. |
| 3,984,574 A | 10/1976 | Comollo |
| 4,139,589 A | 2/1979 | Beringer et al. |
| 4,163,777 A | 8/1979 | Mitra |
| 4,238,475 A | 12/1980 | Witzel et al. |
| 4,276,890 A | 7/1981 | Fichera |
| 4,311,691 A | 1/1982 | Fichera |
| 4,515,769 A | 5/1985 | Merritt et al. |
| 4,555,407 A | 11/1985 | Kramer et al. |
| 4,581,234 A | 4/1986 | Cherukuri et al. |
| 4,587,125 A | 5/1986 | Cherukuri et al. |
| 4,620,982 A | 11/1986 | Serpelloni |
| 4,639,368 A | 1/1987 | Niazi et al. |
| 4,671,953 A | 6/1987 | Stanley et al. |
| 4,711,784 A | 12/1987 | Yang |
| 4,724,151 A | 2/1988 | Mansukhani et al. |
| 4,740,376 A | 4/1988 | Yang |
| 4,751,294 A | 6/1988 | Jackson |
| 4,775,537 A | 10/1988 | Calabro et al. |
| 4,806,356 A | 2/1989 | Shaw |
| 4,808,418 A | 2/1989 | Zamudio-Tena et al. |
| 4,822,597 A | 4/1989 | Faust et al. |
| 4,832,994 A | 5/1989 | Fey |
| 4,842,870 A | 6/1989 | Dokuzovic et al. |
| 4,855,326 A | 8/1989 | Fuisz |
| 4,863,737 A | 9/1989 | Stanley et al. |
| 4,872,884 A | 10/1989 | Cherukuri et al. |
| 4,882,175 A | 11/1989 | Ream et al. |
| 4,907,605 A | 3/1990 | Ray et al. |
| 4,915,958 A | 4/1990 | Faust et al. |
| 4,946,853 A | 8/1990 | Bannon et al. |
| 4,948,595 A | 8/1990 | Patel et al. |
| 4,954,353 A | 9/1990 | Cherukuri et al. |
| 4,963,369 A | 10/1990 | Song et al. |
| 4,967,773 A | 11/1990 | Shaw |
| 4,971,079 A | 11/1990 | Talapin et al. |
| 4,971,806 A | 11/1990 | Cherukuri et al. |
| 4,975,270 A | 12/1990 | Kehoe |
| 4,981,698 A | 1/1991 | Cherukuri et al. |
| 4,983,378 A | 1/1991 | Parnell |
| 4,985,252 A | 1/1991 | Jung et al. |
| 4,986,991 A | 1/1991 | Yatka et al. |
| 4,992,280 A | 2/1991 | Yung Chu et al. |
| 5,004,595 A | 4/1991 | Cherukuri et al. |
| 5,013,716 A | 5/1991 | Cherukuri et al. |
| 5,048,544 A | 9/1991 | Mascarelli et al. |
| 5,069,904 A * | 12/1991 | Masterson .................... 424/401 |
| 5,075,291 A | 12/1991 | DuRoss |

(Continued)

FOREIGN PATENT DOCUMENTS

| | | |
|---|---|---|
| CA | 2109895 | 5/1995 |
| EP | 324981 | 7/1989 |

(Continued)

OTHER PUBLICATIONS

R. Nemeth-Coslett, et al., "Nicotine gum: dose-related effects on cigarette smoking and subjective ratings," Psychopharmacology (1987) 92:424-430.
R. Nemeth-Coslett, et al., "Nictone gum: chew rate, subjective effects and plasma nicotine, Pharmacology Biochem. & Behavior," vol. 29, pp. 747-751 (1988).
J.E. Henningfield, et al., "Drinking coffee and carbonated beverages blocks . . . nicotine polacrilex gum," JAMA, Vo. 264, No. 12 (Sep. 26, 1990).
J. E. Henningfield, et al., "Abuse liability and pharmacodynamic characteristics of . . . inhaled nicotine," J. of Pharmacology & Experimental Therapeutics, vol. 234 (1985).
M.R. Rassing, "Chewing gum as a drug delivery system," Advanced Drug Delivery Reviews, 13 (1994) 89-121.

(Continued)

*Primary Examiner* — Frederick Krass
*Assistant Examiner* — Adam C Milligan
(74) *Attorney, Agent, or Firm* — Berenato & White, LLC

(57) ABSTRACT

A method is provided of making a medicinal delivery system which satiates a craving in an individual when the medicinal delivery system is administered orally to the individual. A coating composition is applied on a saliva-soluble powder to establish a coated powder, the coating composition featuring an at least partially solubilized craving satiation medicinal compound. The coated powder is combined with an edible carrier base to establish a medicinal delivery system that rapidly releases medicine and buffer preferably followed by slower, sustained release.

20 Claims, 6 Drawing Sheets

(56) References Cited

U.S. PATENT DOCUMENTS

| | | |
|---|---|---|
| 5,100,678 A | 3/1992 | Reed et al. |
| 5,110,607 A | 5/1992 | Yang |
| 5,122,127 A | 6/1992 | Stanley |
| 5,132,114 A | 7/1992 | Stanley et al. |
| 5,135,753 A | 8/1992 | Baker et al. |
| 5,139,787 A | 8/1992 | Broderick et al. |
| 5,139,798 A | 8/1992 | Yatka et al. |
| 5,147,648 A | 9/1992 | Bannert et al. |
| 5,147,654 A | 9/1992 | Place et al. |
| 5,149,521 A | 9/1992 | Hirose et al. |
| 5,154,927 A | 10/1992 | Song et al. |
| 5,154,939 A | 10/1992 | Broderick et al. |
| 5,169,657 A | 12/1992 | Yatka et al. |
| 5,169,658 A | 12/1992 | Yatka et al. |
| 5,178,850 A | 1/1993 | DuRoss |
| 5,227,182 A | 7/1993 | Song et al. |
| 5,236,721 A | 8/1993 | Yung Chu et al. |
| 5,244,668 A | 9/1993 | Snipes |
| 5,266,336 A | 11/1993 | McGrew et al. |
| 5,288,497 A | 2/1994 | Stanley et al. |
| 5,288,498 A | 2/1994 | Stanley et al. |
| 5,302,394 A | 4/1994 | Beahm |
| 5,312,626 A | 5/1994 | Gergely et al. |
| 5,334,390 A | 8/1994 | Solomon et al. |
| 5,362,496 A | 11/1994 | Baker et al. |
| 5,364,627 A | 11/1994 | Song |
| 5,380,535 A | 1/1995 | Geyer et al. |
| 5,397,580 A | 3/1995 | Song et al. |
| 5,399,354 A | 3/1995 | Ells et al. |
| 5,405,623 A | 4/1995 | Barkalow et al. |
| 5,437,872 A | 8/1995 | Lee |
| 5,462,754 A | 10/1995 | Synosky et al. |
| 5,486,362 A | 1/1996 | Kitchell et al. |
| 5,486,366 A | 1/1996 | Song et al. |
| 5,487,902 A | 1/1996 | Andersen et al. |
| 5,488,962 A | 2/1996 | Perfetti |
| 5,523,097 A | 6/1996 | Song et al. |
| 5,525,351 A | 6/1996 | Dam |
| 5,543,160 A | 8/1996 | Song et al. |
| 5,543,424 A | 8/1996 | Carlsson et al. |
| 5,545,416 A | 8/1996 | Broderick et al. |
| 5,547,972 A | 8/1996 | Clegg et al. |
| 5,549,906 A | 8/1996 | Santus |
| 5,554,380 A | 9/1996 | Cuca et al. |
| 5,562,936 A | 10/1996 | Song et al. |
| 5,567,450 A | 10/1996 | Zuromski et al. |
| 5,573,774 A | 11/1996 | Keenan |
| 5,596,007 A | 1/1997 | Keenan et al. |
| 5,612,071 A | 3/1997 | Song et al. |
| 5,679,389 A | 10/1997 | Wong et al. |
| 5,711,961 A | 1/1998 | Reiner et al. |
| 5,721,257 A | 2/1998 | Baker et al. |
| 5,725,865 A | 3/1998 | Mane et al. |
| 5,733,574 A | 3/1998 | Dam |
| 5,762,963 A | 6/1998 | Byas-Smith |
| 5,773,053 A | 6/1998 | Song et al. |
| 5,780,051 A | 7/1998 | Eswara et al. |
| 5,783,207 A | 7/1998 | Stanley et al. |
| 5,785,989 A | 7/1998 | Stanley et al. |
| 5,800,847 A | 9/1998 | Song et al. |
| 5,824,334 A | 10/1998 | Stanley et al. |
| 5,834,002 A | 11/1998 | Athanikar |
| 5,837,257 A | 11/1998 | Tsai et al. |
| 5,843,466 A | 12/1998 | Mane et al. |
| 5,846,557 A | 12/1998 | Eisenstadt et al. |
| 5,855,908 A | 1/1999 | Stanley et al. |
| 5,869,503 A | 2/1999 | Keenan |
| 5,869,505 A | 2/1999 | Keenan |
| 5,908,614 A | 6/1999 | Montgomery |
| 5,908,645 A | 6/1999 | Townsend et al. |
| 5,912,007 A | 6/1999 | Pan et al. |
| 5,935,604 A | 8/1999 | Illum |
| 5,955,098 A | 9/1999 | Dugger, III |
| 5,955,099 A | 9/1999 | White |
| 5,955,107 A | 9/1999 | Augello et al. |
| 5,976,581 A | 11/1999 | Song et al. |
| 5,977,166 A | 11/1999 | Greenberg |
| 6,004,589 A | 12/1999 | Song et al. |
| 6,010,723 A | 1/2000 | Song et al. |
| 6,017,565 A | 1/2000 | Rancich et al. |
| 6,030,647 A | 2/2000 | Song et al. |
| 6,086,925 A | 7/2000 | Song et al. |
| 6,110,495 A | 8/2000 | Dam |
| 6,153,629 A | 11/2000 | Hoie |
| 6,177,096 B1 | 1/2001 | Zerbe et al. |
| 6,211,194 B1 | 4/2001 | Westman |
| 6,238,710 B1 | 5/2001 | Song et al. |
| 6,248,760 B1 | 6/2001 | Wilhelmsen |
| 6,264,981 B1 | 7/2001 | Zhang et al. |
| 6,274,778 B1 | 8/2001 | Moraly et al. |
| 6,312,713 B1 | 11/2001 | Korol et al. |
| 6,344,222 B1 | 2/2002 | Cherukuri et al. |
| 6,358,060 B2 | 3/2002 | Pinney et al. |
| 6,365,789 B2 | 4/2002 | Moraly et al. |
| 6,436,371 B2 | 8/2002 | Kilcullen |
| 6,531,154 B1 | 3/2003 | Mathiowitz et al. |
| 6,586,023 B1 | 7/2003 | Song et al. |
| 6,586,449 B1 | 7/2003 | Walling |
| 6,627,234 B1 | 9/2003 | Johnson et al. |
| 6,893,654 B2 | 5/2005 | Pinney et al. |
| 2004/0194793 A1 | 10/2004 | Lindell et al. |
| 2006/0073189 A1 | 4/2006 | Pinney et al. |
| 2006/0110331 A1 | 5/2006 | Dang et al. |
| 2007/0269386 A1 | 11/2007 | Steen et al. |
| 2007/0269492 A1 | 11/2007 | Steen et al. |
| 2008/0020050 A1 | 1/2008 | Chau et al. |

FOREIGN PATENT DOCUMENTS

| | | |
|---|---|---|
| GB | 2230439 | 10/1990 |
| GB | 2 255 892 | 11/1992 |
| GB | 2 299 756 | 10/1996 |
| WO | WO 9320821 | 10/1993 |
| WO | WO 9512399 | 5/1995 |
| WO | WO 9710162 | 3/1997 |
| WO | WO 9742941 | 5/1997 |
| WO | WO 9741858 | 11/1997 |
| WO | WO 01/30288 | 5/2001 |
| WO | WO 01/89476 | 11/2001 |
| WO | WO 02/074238 | 9/2002 |
| WO | WO 02/102357 | 12/2002 |
| WO | WO 03/092591 | 11/2003 |
| WO | WO 2004/056363 | 7/2004 |
| WO | WO 2004/056363 A2 | 7/2004 |
| WO | WO 2004/056363 A3 | 7/2004 |
| WO | WO 2006/058536 | 6/2006 |
| WO | WO 2006/100075 | 9/2006 |
| WO | WO 2006/128468 | 12/2006 |
| WO | WO 2007/104573 | 9/2007 |
| WO | WO 2007/104574 | 9/2007 |
| WO | WO 2007/104575 | 9/2007 |
| WO | WO 2007/133140 | 11/2007 |
| WO | WO 2007/133141 | 11/2007 |

OTHER PUBLICATIONS

J.E. Hennnigfield, et al., "Nicotine dependence: interface between tobacco and tobacco-related disease," Chest, 93:2, 37S-55S (1988).
Office Action dated Apr. 26, 2010 for U.S. Appl. No. 12/026,303.

* cited by examiner

MEDICINAL DELIVERY SYSTEM, AND RELATED METHODS

CROSS REFERENCE TO RELATED APPLICATION AND CLAIM TO PRIORITY

This application is based on provisional application Ser. No 60/832,127, filed Jul. 21, 2006, for John M. Pinney et al., the disclosure of which is incorporated herein by reference and to which priority is claimed under 35 U.S.C. §119(e).

FIELD OF THE INVENTION

Embodiments of the invention relate to a medicinal delivery system containing an edible carrier such as a chewing gum or lozenge, and an active ingredient present in sufficient amount and releasable at a sufficient rate to satiate and relieve a craving. Other embodiments relate to methods of making the medicinal delivery system, and methods of administering the medicinal delivery system to an individual in need of satiation of and relief from a craving. In preferred embodiments, the medicinal delivery system includes a nicotine active ingredient for satiation of and relief from smoking cravings due to nicotine withdrawal.

BACKGROUND OF THE INVENTION

Nicotine is a highly addictive chemical present in cigarettes and other tobacco products, including smokeless tobacco products. Cigarettes are broadly considered the prototypic form of the most addictive and harmful type of tobacco product, however, addiction can develop to all presently known types of nicotine containing tobacco products, and all can be harmful. Therefore, although "cigarettes" and "smoking" are discussed throughout this disclosure, the principles and application of the resulting medicinal formulation apply to all forms of tobacco use and addiction.

Most cigarette smokers find achieving and maintaining prolonged smoking abstinence to be difficult. Research has indicated that abstaining smokers experience periodic and episodic peaks or surges of chronic craving, typically evoked by internal or external stimuli. Persons attempting to quit cigarette smoking often fail in their attempts and suffer from relapse due to the overwhelming intensity of these episodic craving peaks. There is, therefore, a need to provide a cigarette substitute which satiates these episodic craving peaks before relapse can occur.

Some acute treatments for countering cravings are behavioral. As an example, it is often recommended that smokers eat or chew something to distract their attention from their nicotine craving. Many smokers find these behavioral treatments ineffective. Also, these behavioral treatments can lead to the development of other problems, such as weight gain due to constant eating.

It has also been proposed that the administration of acute doses of nicotine could satisfy cravings, much in the manner that smoking a cigarette satiates a nicotine-withdrawal craving. Nicotine delivery systems containing actives for oral administration now include various chewing gum and lozenge formulations. Chewing gums permit release of nicotine over time as the gum product is masticated, or chewed. The action of saliva on the gum or lozenge upon ingestion further facilitates release of nicotine, as well as its subsequent absorption by the mucous membranes lining the mouth, throat, larynx and esophagus.

Nicotine is a weak base with a pKa of approximately 8.0. Absorption of nicotine into the bloodstream from the oral mucosa is highly dependent upon the concentration of un-ionized nicotine. Only un-ionized nicotine can be absorbed through the oral mucosa. Ionized nicotine cannot be absorbed and will be swallowed and mostly lost during transit through the gastrointestinal tract. Efficient mucosal absorption of nicotine may be facilitated by addition of a buffer to the gum to convert ionized nicotine to un-ionized nicotine. For example, without buffer, at a normal saliva pH of 6.5, only 3% of the available nicotine is in the un-ionized form which can be absorbed, whereas, at a buffered saliva pH of 9.0, approximately 91% of the available nicotine is in an un-ionized state which can be absorbed transmucosally. Buffer and nicotine incorporated into gum are released at the same time during chewing. An effective buffer raises the pH of saliva from a pH of approximately 6-7 to a pH of approximately 8-11. The buffer converts ionized nicotine to un-ionized nicotine that can be absorbed into the bloodstream. Thus, efficient delivery of nicotine to the bloodstream is a function of the efficiency of nicotine release and the efficiency of buffer to convert ionized nicotine to un-ionized nicotine.

A commercially available nicotine delivery gum is marketed under the trademark NICORETTE®. This commercially available gum utilizes the "chew and park" method for providing nicotine release. The consumer bites down on a piece of gum until sensing a "tingle", then parks the gum inside the mouth for a period, and then repeats this regimen to obtain further release of nicotine. Nicotine is released in a steady, slow manner, and thus is highly dependent on conscious chewing actions by the user.

Nicotine released from NICORETTE reaches the bloodstream in several different ways. About 50% of the nicotine from the 2 and 4 milligram versions of NICORETTE is released from the gum during chewing. The rest of the nicotine typically remains in the gum and is discarded by the user. Of the nicotine delivered by the 2 milligram version of the NICORETTE gum to the saliva, about 0.8 milligram may be absorbed through the membranes of the mouth (the buccal mucosa) and appear in the bloodstream. The remaining approximately 0.2 milligram is swallowed, of which 0.06 milligram survives the first pass effects of hepatic metabolism and appears in the bloodstream. The 4 milligram version of NICORETTE gum achieves nicotine absorption values which are approximately twice those of the 2 milligram version.

Because of slow nicotine release and weak buffering action, it takes approximately 10 to 30 minutes after ingestion to achieve adequate blood levels of nicotine from NICORETTE, regardless of whether the user practices the "chew and park" (or "bite and park") method or chews at regular intervals (e.g., one chew per 4 seconds) to relieve cravings. Although the amount of nicotine absorption from NICORETTE is related to the chewing rate and the time the saliva is held in the mouth, these variables are significant only at the extremes of rapid versus slow chewing action, and frequent versus infrequent swallowing. Outside of such extremes, these variables have very little impact on nicotine absorption.

The critical period of delay immediately following the onset of a craving, i.e., during the episodic craving peak or event, is the time the smoker experiencing a craving would normally choose to smoke a cigarette to access nicotine for relieving the craving. A product that delivers nicotine too slowly will be ineffective in relieving or satisfying the episodic craving peak or event. For example, in the case of NICORETTE, a delay of 10 minutes or more in the release and absorption of a nicotine dose comparable to the amount of nicotine derived from a cigarette may be excessively long to wait for someone who is trying to quit smoking. In practice, most commercial products simply fail to deliver an adequate dosing of the medication, especially early in the administration process, i.e., within a few minutes of administration. The result many times is a product that the smoking customer seeking to abstain from smoking finds highly ineffective in satiating his or her cravings. As a consequence, the smoker will succumb to the craving by turning to a cigarette before the medicinal nicotine delivery system has released adequate nicotine to satiate the craving.

There is consequently a need in the art for an improved delivery system for actives such as nicotine. More specifically, there is a need for an improved medicinal delivery system that provides a rapid release rate for nicotine or other medicines early in the ingestion (e.g., chewing) process, together with adequate buffering, to simulate the nicotine release of a cigarette and quench the craving of the abstaining smoker. Following an initial phase of rapid release, there is preferably a sustained release of medicine. The rapid release of medicine followed by a sustained release is referred to herein as "bi-phasic release". There is a need in the art for a nicotine delivery product which is highly efficacious in releasing a specified, effective quantity of the active ingredient shortly after administration to provide the user with adequate blood levels of nicotine soon after onset of ingestion for suppression of cravings and withdrawal symptoms followed by sustained release of some or all of the remaining dose.

A rapid achievement of adequate blood levels of nicotine, preferably over the first five minutes of oral manipulation (e.g., chewing) would move the product toward a closer approximation of the nicotine blood levels delivered by smoking a cigarette. With a formulation that rapidly releases amounts of nicotine and buffer, preferably over the first five minutes of oral manipulation in a form that is readily absorbed into the bloodstream, the smoker can satiate and obtain relief from cravings quickly, before episodic craving peaks or events drive the smoker into relapse.

SUMMARY OF THE INVENTION

According to a first aspect of the invention, a method is provided of making a medicinal delivery system that delivers medicine which satiates a craving in an individual experiencing nicotine withdrawal when the medicinal delivery system is administered orally to and orally manipulated by the individual. The method features applying a coating composition on a saliva-soluble powder to establish a coated powder, the coating composition comprising an at least partially solubilized craving-satiation medicinal compound, and combining the coated powder with an edible carrier base, such as a chewing gum or lozenge base, and buffer to establish a medicinal delivery system.

A second aspect of the invention provides a method of satiating a craving in an individual, in which a medicinal delivery system is administered to an individual in need of a craving satiation. The medicinal delivery system is made by applying a coating composition on a saliva-soluble powder to establish a coated powder, and combining the coated powder with a carrier base, such as a chewing gum or lozenge base, and buffer to establish the medicinal delivery system. The coating composition features an at least partially solubilized craving satiation medicinal compound.

According to a third aspect of the invention, a medicinal delivery system is provided. The system features an edible carrier, such as a chewing gum or lozenge base, a buffer, and a saliva-soluble powder coated with a craving-satiation compound. In a preferred embodiment, the craving-satiation compound comprises nicotine.

A fourth aspect of the invention provides a method of making a nicotine-satiation delivery system which satiates smoking cravings in an individual in need of nicotine-craving relief when the nicotine-satiation delivery system is administered orally to and orally manipulated (e.g., masticated) by the individual. The method features applying a coating composition on a saliva-soluble powder, and combining the coated powder with an edible carrier base, such as a chewing gum or lozenge base, and buffer to establish the nicotine-satiation delivery system. The coating composition features an at least partially solubilized nicotine compound.

According to a fifth aspect of the invention, a method is provided of satiating a smoking craving in an individual, comprising administering a medicinal delivery system to an individual in need of a smoking-craving relief, for example, a person practicing abstinence from smoking. The medicinal delivery system is made by applying a coating composition on a saliva-soluble powder, and combining the coated powder with an edible base, such as a chewing gum or lozenge base. The composition features an at least partially solubilized nicotine compound.

In preferred yet optional embodiments of the above-described aspects of the invention, the coated powder and the buffer system are substantially uniformly and homogenously distributed in the gum or lozenge base, for example, by thorough mixing, for rapid release along with nicotine.

In preferred embodiments of the above-described aspects, rapid release of medicine is obtained over the first five minutes following the onset of ingestion, e.g., mastication, of the medicinal delivery system, optionally yet preferably followed by a less rapid sustained release of medicine over a 5-20 minute, more preferably a 10-20 minute period. This pattern of release is referred to as bi-phasic release of medication. The product rapidly releases buffer over the first five minutes, thus facilitating rapid absorption of medication. The combination of rapid release of medicine and buffer followed by sustained release insures rapid absorption of the medicine and rapid and sustained relief of craving.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In such drawings.

DETAILED DESCRIPTION OF EMBODIMENTS OF THE INVENTION

Reference will now be made in detail to the presently preferred embodiments and methods of the invention as illustrated in the accompanying drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

Unless otherwise stated, all percentages provided herein are weight percentages, based on the total weight of the medicinal delivery composition, except where noted otherwise.

Figure 1:
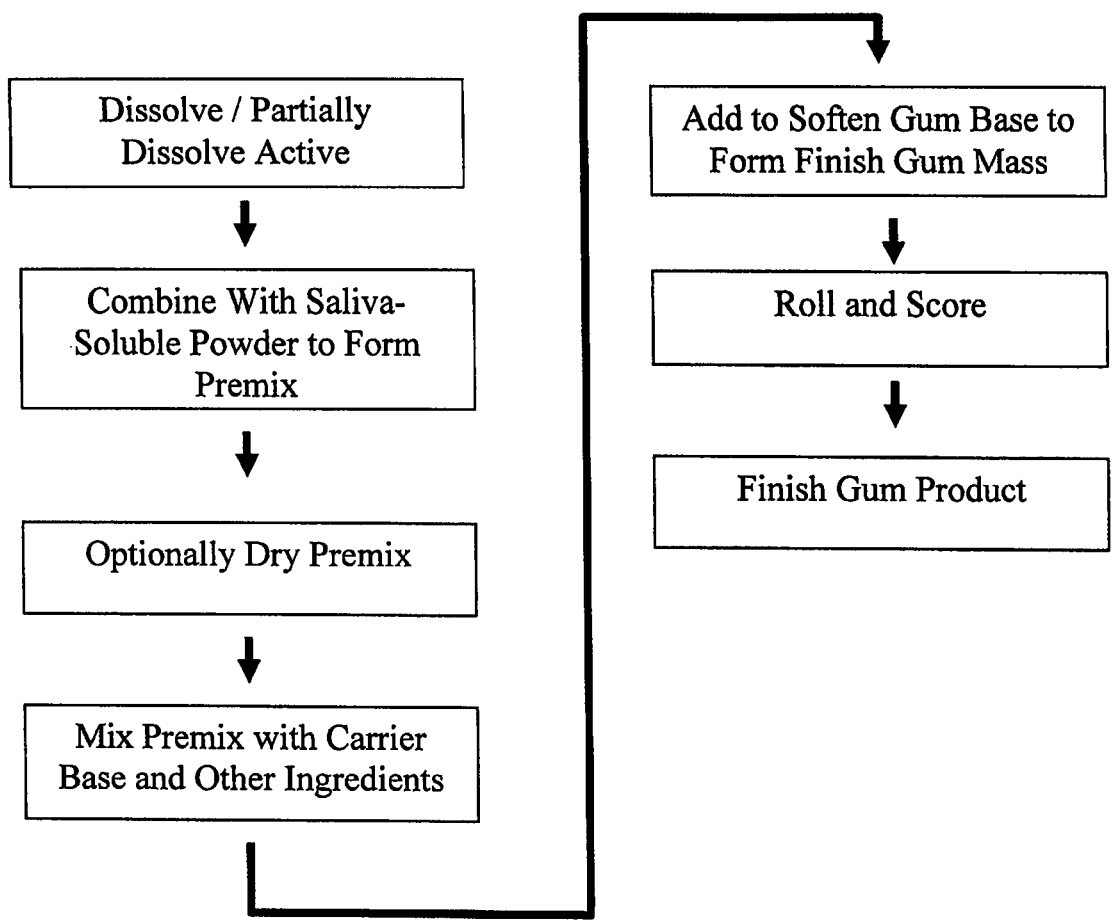
FIG. 1 is a flow diagram of a method of making medicinal delivery system according to an embodiment of the invention.

A method of making a medicated and buffered delivery system for craving satiation according to an embodiment of the invention is now described in detail with reference to FIG. 1. At least one craving-satiation compound is at least partially dissolved in a suitable solvent or solvents. As referred to herein, the phrase "at least partially dissolved" should be understood to encompass dissolution (also referred to as solubilization) of the craving-satiation compound in a solvent, and may encompass formation of a free-flowing liquid or a semi-liquid, such as a suspension, emulsion, or paste. The phrase "at least partially" also encompasses complete dissolution of the craving-reduction compound.

The particular solvent selected will depend upon its ability to dissolve the craving-satiation compound and its compatibility with the process. Polar solvents such as water and lower alkanols (e.g., ethanol) are particularly preferred for solubilizing nicotine. A solubilized bulk sweetener solution, especially a sugar alcohol such as a sorbitol solution, is especially preferred for partially dissolving the craving-satiation medicinal compound into a paste. In the event bulk sweeteners are selected as the saliva-soluble powder and for the solvent solution, the bulk sweetener in the solvent solution may be the same as or different from the bulk sweetener selected as the saliva-soluble powder.

At least one bulk sweetener preferably is highly soluble in water. Optionally, additional bulk sweeteners having moderate or low solubility in water may also be included in the premix. The high solubility is desired so that the selected bulk sweetener(s) will dissolve quickly in the mouth of the recipient upon mastication of the chewing gum or absorption (e.g., via sucking) of the lozenge, releasing the medicinal craving-satiating compound applied as a coating to the powder of the premix. The following solubility data for sugar alcohols is reported by Schiwek, H. in Ullman's Encyclopedia of Industrial Chemistry, $5^{th}$ ed. Vol. A25, Sugar Alcohols, (1994). It is preferred that the sugar alcohol solution, if selected, be selected from a sugar alcohol having a solubility of at least 50, more preferably at least about 65, and still more preferably at least about 70 grams of sugar alcohol dissolved per 100 grams of water.

TABLE 1

| Sugar Alcohol | Solubility (grams/100 grams water) |
|---|---|
| Mannitol | 23 |
| Isomalt | 38 |
| Lactitol | 55 |
| Maltitol | 71 |
| Xylitol | 70 |
| Sorbitol | 75 |

The solubilized craving-satiation compound is then coated onto a saliva-soluble powder. Coating may be performed at room temperature. Standard coating equipment and procedures may be employed for coating the craving-satiation compound on the powder. The coated saliva-soluble powder is also referred to herein as a "premix." It should be understood that the premix may contain additional ingredients, although any such additional ingredients preferably will not adversely affect the coating of the active onto the saliva-soluble powder. Preferably, the premix is free of components that are insoluble in saliva. The solvent optionally may be removed, such as by evaporation or otherwise, before or more preferably after the active has been coated on the powder. The entire process of complete or partial dissolution of a craving-satiation compound in a solvent, coating onto a saliva-soluble powder, and solvent removal to form the "pre-mix" is herein referred to as "solvent treatment".

Without wishing to be bound by any theory, it is believed that the "solvent treatment" of nicotine during preparation of the premix alters the crystalline form of the nicotine to either another crystalline form or, more likely, to an amorphous state which is more readily solubilizable during ingestion to promote a high initial nicotine release rate. Again not wishing to be bound by theory, it is further believed that coating the nicotine on a saliva-soluble, water-soluble powder such as sorbitol improves the rapid release of the nicotine, thereby increasing performance of the delivery system. Dissolution of the powder during mastication or other ingestion creates a liquid medium that can entrain and wash out the nicotine and buffer from the gum or lozenge rapidly. The nicotine becomes available for absorption by the user more quickly in this manner. As discussed below, the rapid availability of the nicotine makes possible nicotine release rates of greater than 45 and even 50 weight percent within 5 minutes of the onset of oral ingestion.

The premix is combined with an edible carrier, such as a gum base or lozenge base, and optionally additional ingredients. The procedures set forth in U.S. Pat. No. 4,405,647 may be especially helpful to the skilled artisan as general guidance for the preparation of the chewing gum delivery system. Briefly stated, the gum base material may be melted or softened using one or more of the softening agents, plasticizers and/or solvents and filler materials. The premix and additional ingredients, such as buffering agents and others described below, are then admixed into the carrier base. The premix may be added to the carrier base at any time during the mixing procedure, including towards the end of the mixing procedures, e.g., after the carrier base material has been mixed with the other components. It is preferred, yet optional, however, that after the addition of the premix sufficient mixing be performed to distribute the premix coated powder substantially homogenously. It should be understood that the pre-mix, carrier base, and additional ingredients may be combined with one another in any sequence.

Mixing optionally is accomplished by comminuting the gum base material together with the water-soluble ingredients in a bed or blender within a gaseous medium at room temperature, as described in the aforementioned U.S. Pat. No. 4,405,647. This material is continuously pulverized and thereby chopped into much smaller particles. To prevent adherence of the resultant particles to one another, additional filler or bulking material may be added like lubricants, glidants and other tableting and compression aids well known in the pharmaceutical industry, such as for example, silica gel or calcium carbonate. Granules of any desired size and shape may be obtained upon the introduction of a standard mesh screen to separate the particulates once formed.

Medicinal Craving-Satiation Compound

The terms medicinal and medicine as used herein are not limited to substances which relieve pain, disease and/or infection. The terms encompass therapeutic substances which can be effectively incorporated into the medicine-delivery system to satiate cravings of the recipient.

The medicinal craving-satiation compound preferably comprises a soluble tobacco alkaloid. Tobacco alkaloids include nicotine and nicotine-like or related pharmacologically active compounds such as nor-nicotine, lobeline and the like, as well as the free base substance nicotine and all pharmacologically acceptable salts of nicotine, including acid addition salts. "Nicotine compounds" as that term is used herein therefore includes all the foregoing tobacco alkaloids. Of these, the nicotine salts are useful and can include, for example, nicotine hydrogen tartrate and nicotine bitartrate dihydrate (NBD), as well as nicotine hydrochloride, nicotine dihydrochloride, nicotine sulfate, nicotine citrate, nicotine zinc chloride monohydrate and nicotine salicylate, nicotine polacrilex, and other nicotine-ion exchange resins, either alone or in combination. Of the foregoing, nicotine hydrogen tartrate and nicotine bitartrate dihydrate may be especially suitable.

A serving of the composition of the invention preferably contains about 0.1 to about 10 milligrams of nicotine (as measured in its free base form) or other craving satiation medicinal compound. More desirably, the amount of nicotine will be within the range of about 1.0 to about 5.0 milligrams, for example in standard dosing units of approximately 2 milligrams and 4 milligrams. As a weight percentage, nicotine (in whatever chosen form, measured as per its free base form) desirably constitutes about 0.1 to about 1.0 weight percent, more preferably about 0.1 to about 0.5 weight percent of the total weight of the medicinal delivery system composition. In the premix, the nicotine preferably constitutes about 1.0 to about 20 weight percent of the total weight of the premix composition. It has been found that a relatively uniform coating of craving-satiation medicinal compound may be obtained on the saliva-soluble powder by practicing the above ranges.

The concentration of active in the composition may be selected to provide an intended dosage or release rate. The desired dosage of nicotine (or other active) selected may depend upon the nature and severity of the craving to be treated, the treatment regime, characteristics (e.g., weight, age, gender) of the recipient, and other factors affecting treatment. Selection of an appropriate active concentration may also take into consideration the particular ingredients selected, such as the potency of the nicotine source or other active utilized, and the nature and amount of solvent.

Additionally, it is contemplated that the skilled artisan may choose to add extra or secondary active, e.g., not contained in the premix but added to the carrier base. The secondary active preferably constitutes no more than about 25 percent of the system total weight. The amount in excess of approximately 10 weight percent may be regarded as overage, that is, the amount which may be expected to be "washed away" or otherwise not released or absorbed during ingestion. An example of a secondary nicotine source is a solid complex of one or more tobacco alkaloid compounds bound to an ion exchange resin or other polymer release system, particularly a cation exchanger. The inclusion of some ion-exchange resin in the formulation may further act synergistically on the nicotine release rate for the nicotine salts. An exhaustive listing of nicotine ion exchange resins and their chemistry is readily available from various sources in the industry, and the skilled artisan may consult Lichtneckert et al., U.S. Pat. No. 3,901, 248, for a further discussion and listing of resins. Nicotine polacrilex as a nicotine ion exchange resin may be especially desirable for use with the composition.

Saliva-Soluble Powder

The saliva-soluble powder is preferably water-soluble and more preferably contains at least one bulk sweetener. Generally, bulk sweeteners impart improved palatability to the composition, and thereby provide a pleasant chewing experience to help in masking the bitter, acrid taste of nicotine. The "sweetener" may or may not be perceptibly sweet. Examples of sweeteners include those compounds selected from the group consisting of saccharide material such as the mono-, di-, tri- and polysaccharide materials available in the industry, including oligomers, and oligosaccharides. As non-limiting examples, sugars such as sucrose, glucose (corn syrup), dextrose, invert sugar, fructose, and mixtures thereof may be useful. Less or non-sweet sugars and polysaccharide materials such as maltodextrin and polydextrose may also be utilized. For certain individuals, such as those concerned about weight gain and tooth decay, "sugar-free" or "non-sucrose" formulations may be especially desirable. Thus, natural and synthetic non-saccharide-based bulk sweeteners may be selected from the group consisting of saccharin and its various salts such as the sodium and calcium salts, cyclamic acid and its various salts, dipeptide sweeteners, chlorinated sugar derivatives such as sucralose, dihydrochalcone, glycyrrhin, Stevia rebaudiana (Stevioside), and sugar alcohols such as sorbitol, sorbitol syrup, mannitol, xylitol, hexa-resorcinol and the like, including mixtures of any of the foregoing, are contemplated for use herein. Hydrogenated starch hydrolysate (lycasin), and the potassium, calcium and sodium salts of 3,6-dihydro-6-methyl-1-1,2,3-oxathiazin-4-one-2,2-dioxide may also be included as sweetener material. Of the foregoing, sorbitol and xylitol are particularly preferred, either alone or more desirably in combination. Xylitol has been reported to possess non-cariogenic or anti-cariogenic properties.

The saliva-soluble powder preferably makes up about 70 to about 97 weight percent of the premix. It should be understood that additional saliva-soluble powder, such as bulk sweeteners (e.g., sorbitol) may be added to the medicate composition apart from the premix, e.g., by direct addition to the carrier base separate from the premix. It is preferred that the total weight of bulk sweetener found in the composition be in a range of about 30 to about 60, more preferably about 40 to about 50 weight percent of the total weight of the formulation.

Preferably, the saliva-soluble powder is in a fine form, for example, with particle sizes of 600 microns or less, and is in a substantially non-agglomerated state prior to receiving a coating in the premix preparation stage.

Carrier Base

Suitable solid carrier bases include, but are not necessarily limited to, chewing gum and lozenges.

Gum Base

The chewing gum comprises a gum base matrix as a major component. The gum base matrix includes at least one gum base material which may be selected from the many water-insoluble and saliva-insoluble gum base materials known in the art. Illustrative examples of suitable polymers for gum bases include both natural and synthetic elastomers and rubbers, as well as mixtures thereof. Naturally-derived polymers include, for example, substances of plant origin like chicle, jelutong, gutta percha and crown gum. Synthetic elastomers such as butadiene-styrene copolymers, isobutylene and isoprene copolymers (e.g., "butyl rubber" in the art), polyethylene, polyisobutylene, polyvinylesters such as polyvinylacetate, and mixtures of any of the foregoing may be particularly useful.

In one embodiment, it is highly preferable that the gum base be selected so as to provide a final chewing gum composition which has a relatively "soft" chew both at the onset of mastication, as well as towards the end of the chewing process, and even as long as about 20 to 30 minutes or so. Another desirable characteristic of the gum base should be its ability to achieve preferred results sought by the present invention, e.g., to facilitate the early release over the first 5 minutes of at least 45 weight percent, more preferably at least 50 weight percent of the active ingredient(s), such as nicotine, as well as early release of sufficient buffer (described below) to raise the pH of mouth saliva to the range of pH 8-10.

In another preferred embodiment of the invention, the type of gum base utilized includes at least some butyl rubber (copolymer of isoprene and isobutylene), with additional amounts of polyisobutylene, and with polyvinylacetate (preferably PVA having a MW of approximately 12,000) also being present. This butyl-rubber based material appears to have certain advantages when used together with nicotine in the form of a salt.

The gum base matrix will typically comprise from about 30 to about 90 weight percent of the total weight of the chewing gum composition of the invention. It is more preferred for the chewing gum base matrix material to constitute less than about 70 percent of the total weight of the chewing gum composition. It is especially preferred for the gum base matrix to constitute from about 35 to about 55 weight percent of the chewing gum composition. Excess gum base may interfere with the release of the active tobacco alkaloid material, and additionally, may contribute to tackiness and poor mouth-feel of the final product.

It is contemplated that about 25 weight percent to about 75 weight percent, e.g., about 30 weight percent to about 60 weight percent, of the gum base matrix consists of the gum base polymer material(s) heretofore described. An exemplary gum base matrix formulation contains polyvinylacetate having a molecular weight of about 12,000 (about 14 weight percent of the total chewing gum composition), polyisobutylene (about 5 weight percent of the total chewing gum composition), and butyl rubber (about 4 weight percent of the total chewing gum composition). Together these polymers may comprise about 35 weight percent to about 45 weight percent of the gum base matrix, e.g., about 40% of the gum base matrix.

The gum base matrix may additionally contain other ingredients well known, such as plasticizers, processing aids, and softeners to help reduce the viscosity of the gum base to a desirable consistency and to improve the overall texture and bite. These compounds are also noted for their emulsifying properties. As non-limiting examples, compounds such as lecithin, mono- and diglycerides, lanolin, stearic acid, sodium stearate, potassium stearate, glycerol triacetate, glycerol monostearate and glycerin are provided. Stearic acid, lecithin and mono- and diglycerides are particularly exemplary. Plasticizers and softeners are desirable as part of the formulation because in addition to softening the primary gum base polymeric compound, they also may facilitate release of the active upon mastication. When added, the plasticizers and softeners may constitute, for example, from about 0.1 to about 20 weight percent of the gum base matrix, and more desirably may constitute about 5 weight percent to about 15 weight percent of the gum base matrix.

Waxes such as beeswax and microcrystalline wax, and fats/oils such as soybean and cottonseed oils are also contemplated as optionally part of the gum base formulation. These compounds also function as softening agents. Typically, these compounds (either alone or in combination) may comprise from zero up to about 25 weight percent of the gum base matrix, and even more desirably will constitute less than about 20 weight percent of the gum base matrix, e.g., about 15 weight percent to about 20 weight percent of the gum base matrix. An especially desirable formulation will include a combination of microcrystalline wax and partially hydrogenated soybean oil in an approximate 1:2 weight ratio. A more exhaustive listing of these compounds, along with recommended weight percentages, may be found in available industry literature.

Softeners also may be included as part of the gum base matrix, especially softeners selected from the group consisting of rosin and resin material typically utilized in the confectionery chewing gum industry. Examples include methyl, glycerol, and pentaerythritol esters of rosins or modified rosins, such as hydrogenated, dimerized or polymerized rosins or mixtures thereof. More specific examples include pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene, and terpene resins including polyterpene and mixtures thereof. Elastomers can comprise from about zero to 75 weight percent of the gum base matrix. It is possible to minimize or even eliminate the quantity of rosin/resin in the gum base.

The gum base matrix may be material as heretofore described, i.e., that which facilitates release of the active (as for example that having a hydrophilic moiety, or a butyl rubber-based moiety), or may be other gum matrix material known in the art. For example, a low-moisture, non-aqueous gum base matrix having a high degree of hydrophobicity may be utilized in certain formulations. In certain situations, the gum base matrix material and the nicotine can have different, somewhat incompatible moieties so that the nicotine is not strongly retained by the gum base matrix, and can be released more easily.

Lozenge Base

As mentioned above, another carrier useful for the present invention is a lozenge. Generally, lozenges are hard candy-like sources of therapeutic compounds. Lozenges usually contain high levels of sweeteners in the form of natural or synthetic sugar substitutes, such as sucrose and corn syrup, or a sugar alcohol such as mannitol, or other sweeteners described herein, as a major component. For example, a candy base material may comprise from about 70 to about 98 weight percent of the total weight of the composition, more preferably from about 80 to about 95 weight percent of the total weight. Lozenges often have tablet or diamond shapes, and are intended to be orally sucked on and dissolved in the mouth of the user. The lozenge may be a hard solid or a soft chew.

Buffer System

Another ingredient preferably included as part of the disclosed medicinal delivery system is a buffering agent or system. Buffering agents are those compounds that assist in release and conversion of the nicotine salts (ionized nicotine) to nicotine free base (unionized nicotine). Passage of actives across the mucous membranes inside the mouth to the bloodstream and to target tissues is due primarily to passive diffusion of the unionized form of the active. To be effective the buffer agent should be released in sufficient amounts with the release of the active to create a basic or alkaline pH environment inside the mouth, thereby facilitating effective delivery to target organs. Consequently, conversion of nicotine into freebase nicotine in mouth saliva is an important step in providing smokers with adequate blood levels of nicotine to satiate cravings. Buffering agents assist with this conversion by raising the pH and thereby facilitating nicotine absorption.

Various salts, for example, sodium carbonate, sodium bicarbonate, potassium carbonate, potassium bicarbonate, potassium citrate and dipotassium phosphate, or mixtures thereof, are particularly preferred buffers. Potassium carbonate alone may be especially desirable as a pH buffering agent, especially with embodiments containing butyl rubber-based gum base. The buffering agent may comprise about 0.1 weight percent to about 10 weight percent of the nicotine delivery system formulation, and desirably will be within the range of about 4.0 weight percent to about 6.0 weight percent thereof. Increasing the buffer will usually result in a higher boost of pH inside the oral cavity within a shorter time period.

In one preferred embodiment of the invention, it is preferable that the buffers be chosen so as to yield a pH in excess of at least about 7.5 inside the mouth, and even more desirably in excess of about 8.0, or even greater than about 8.5. A pH level of at least about 9.0 is particularly preferred inside the mouth within about 10 minutes, more preferably within about 5 minutes from the onset of absorption/mastication. Even more desirable is a pH of at least about 9.0 within about 3 minutes, and especially within about 1 minute. In addition to facilitating absorption of nicotine inside the mouth, the buffer system is preferably optimized in conjunction with the other components so that it does not result in excessive, premature (i.e., before pH adjustment by the buffer) release of nicotine inside the mouth which would overwhelm the user. The ideal pH level may depend on the chemical properties (e.g., pKa) of the active medicine and the desired speed of absorption. The quantity and type of buffer materials furthermore should not cause unpleasant organoleptic side effects, such as irritation, burning, coughing or choking, etc.

Fillers

Fillers may also be present in or added to the carrier base matrix as part of the composition of the invention. In the case of a chewing gum carrier, the filler material optionally is selected to enhance the chewability of the final chewing gum composition. In at least some embodiments, certain filler material may also enhance the release and absorption of nicotine and other tobacco alkaloids. Those fillers which are substantially non-reactive with other components of the final formulation are preferred. Desirable filler materials may include calcium carbonate, magnesium silicate (talc), as well as dicalcium phosphate, and any mixtures thereof. Particularly preferred may be dicalcium phosphate. Other metallic mineral salts may also be utilized as filler material, such as for example alumina, aluminum hydroxide, and aluminum silicates, provided they possess the characteristics heretofore set forth. Filler material, when present, will typically comprise about 0.1 to about 30 weight percent of the carrier base, and more preferably will be within the range of about 10 to about 20 weight percent thereof.

Flavoring and Coloring Agents

In addition to the bulk sweetening material, the composition of the invention also optionally comprises one or more flavoring agents. The flavoring agents may be selected from any of the industry-available natural and synthetically-derived food and pharmaceutical flavors. Especially preferred are those materials which impart a cooling and/or vaporizing sensation to the consumer upon ingestion of the gum or lozenge. As non-limiting examples, peppermint, spearmint, wintergreen, cinnamon, menthol and menthone flavors, oils and derivatives are desirable. Other compounds are contemplated as well which may impart a physiological or psychological calming or cooling sensation to the user who is trying to quit smoking. Those flavors which mimic the taste of tobacco are also within the scope of the invention. Food and pharmaceutical grade coloring agents available throughout the industry may also be utilized. Any of the foregoing flavor and coloring agents, either alone or in combination will typically comprise from about 0 to about 10 weight percent of the carrier composition, more preferably from about 0.1 to about 5 weight percent, and even more desirably about 2 to about 3 weight percent of the carrier composition. It is also within the scope of the invention for the formulation to specifically omit any adjunct flavors or colors. These embodiments may be preferred to avoid making the final product in any way attractive or enticing to non-smokers and especially children.

Additives and Other Materials

Also optionally included as part of the medicinal delivery system embodied herein is one or more of non-cariogenic, anti-cavity and tooth-whitening ingredients. These are preferably utilized with the non-cariogenic sweeteners heretofore described. U.S. Pat. No. 5,762,911 describes anti-cariogenic agents such as calcium salts, arginine and a cariostatic anion such as an organic phosphate compound. Tooth-whitening compounds include, for example, kaolin, calcium carbonate, silicon dioxide and certain cellulosic materials. These may be included in the final formulation in amounts of from about 0 to about 10 percent by weight, and more preferably from about 0 to about 3 weight percent.

Trace amounts of standard industry preservatives such as butylated hydroxy toluene (BHT) may also be present in amounts less than about 0.1% or so of the carrier base.

Products and Product Characteristics

An exemplary implementation of the present invention as a medicinal delivery system is designed to permit a rapid and highly reliable release of active medicine inside the body and especially in the mouth and buccal cavity. While other forms may be contemplated by those skilled in the art and are within the scope set forth herein, the medicine delivery system is preferably in the form of a chewing gum. It is particularly preferred that the medicated chewing gum delivery system comprise a chewing gum base mixed with a saliva-soluble powder coated with a craving-satiation compound.

The medicinal delivery system may be formulated into any desired shape or size. Preferably, gum-based medicinal delivery systems will take the shape of sticks or tabs, or any other form, such as those which are typically utilized by chewing gum manufacturers. Lozenges typically take the form of tablets, but may be shaped into various objects. Each serving may be coated with an edible confectionery-type shell. Optionally, the shell may contain a craving-satiation agent, such as nicotine, and/or any of the non-active ingredients (e.g., buffering agent) mentioned herein.

Other possible physical embodiments of the medicinal delivery system of the invention include, for example, various centerfill configurations. In the center-fill embodiments the gum base or lozenge base composition will at least partially surround a centerfill. The centerfill may be a liquid or semi-liquid material. The centerfill material may be an active ingredient or a non-active, such as buffers, sweeteners and/or flavorants as heretofore described. A combination of saccharide material, flavoring, polyol and edible gel material is one example of a centerfill. The centerfill embodiments may be prepared using methods known in the confectionery and chewing gum industries, such as the method described in U.S. Pat. No. 3,806,290. Other methods of forming centerfill lozenges and chewing gum known in the art may also be utilized.

Craving Treatment and Efficacy

The delivery system of the invention can be used for a variety of therapeutic purposes including as part of a smoking cessation or reduction program, or as a smoking alternative as in situational circumstances dictating abstinence, such as for satiating a craving in a smoke free environment (e.g., on a plane, public transportation, smoke-free offices, etc.). According to a contemplated treatment regime, a serving size piece of the delivery system is introduced into the mouth, the user chews the gum or digests the lozenge as is normally done with any non-medicated type of carriers for at least 5 minutes, and optionally up to about 20 minutes to about 30 minutes or more. Chewing rate is not particularly limited, but an approximately average rate of about 10-30 chews per minute is contemplated. The gum is then discarded, whereas lozenges are usually dissolved in the mouth and swallowed. This process is repeated as long as nicotine cravings arise or the risk of smoking is present. Care should be exercised, however, to avoid overdosing on this smoking substitute. A serving of the nicotine delivery system of the invention is designed to cause a loaded nicotine concentration level in the bloodstream of at least about 2 to 7 nanograms of nicotine per milliliter of blood. More preferably, at least about 3 ng/mL nicotine will be attained, and more preferably at least about 5 ng/mL. If desired, the present invention can attain a nicotine concentration of 10 ng/mL in the bloodstream.

The combination of active(s), buffer(s) and inert ingredient(s) constituting the nicotine delivery system composition of the invention together result in a formulation which is highly effective as a smoking substitute for satiating nicotine cravings and relieving withdrawal pains. The formulations in preferred embodiments deliver at least about 45%, and more preferably at least about 50% of its nicotine content in a suitable form for absorption within about 5 minutes of ingestion. In this way, a smoker's physiological need for the drug is sated quickly, just as would be accomplished by smoking a cigarette. In particular, a smoker generally drags more strongly on a cigarette during the initial 1-2 minutes of smoking, extracting a high initial load of nicotine to quickly sate his or her physiological cravings. The nicotine-satiation system of the invention preferably provides an initial nicotine release rate that is comparable to the intensity of the cigarette drag over a five minute period, thereby satiating the episodic event.

It is also preferred that subsequent to this initial rapid release phase, the nicotine delivery system settle into a less rapid, continuous release for at least about an additional 10 minutes, still more preferably at least about an additional 25 minutes. The release of active during this continuous phase may be relatively uniform.

Advantageously, the release of nicotine is substantially but preferably not completely independent of the actual ingestion rate. For example, in the case of a chewing gum base, active release will occur whether the composition is chewed continuously, or whether the "chew and park" method is utilized. Thus, the consumer does not have to be particularly conscious of his/her chewing action in order to effectively receive nicotine. However, at the same time, the release rate will be affected somewhat by the rate of mastication. If chewers feel a continuing need for nicotine after a number of minutes, they can chew more rapidly, whereas if they feel their cravings subsiding, they can chew more slowly, and thereby release less nicotine. Consequently, the product is still responsive to the needs of the chewer, who can adjust intake of nicotine to match their cravings. The same holds true with lozenges, which can be manipulated by the tongue or sucked more vigorously by the user to increase lozenge dissolution and increase nicotine dosing.

Without wishing to be bound by any theory, it is believed that the high initial release rate of nicotine attainable by the present invention is due, at least in part, to the "solvent treatment" of nicotine during preparation of the premix. The "solvent treatment" disperses the nicotine over the relatively large surface area of the saliva-soluble powder, making the nicotine readily available for release and absorption into the blood stream. It is further believed that the solvated nicotine undergoes a change in its crystalline form, perhaps transforming to an amorphous state, which is believed to further promote the release and absorption of the nicotine. Finally, because the powder is rapidly dissolved in saliva, it provides a fluid medium for entraining and carrying the nicotine or other active out of the gum for absorption by the chewer.

Rate of nicotine release may be measured using the following procedure. Individual, weighed pieces of the nicotine release system (e.g., gum) are chewed by participants either ad lib (at the participant's preferred chew rate) or at a scheduled rate (e.g., using a metronome). Individual pre-weighed pieces are chewed or digested for a predetermined time (e.g., 3, 5, 10, 20, 30 minutes) while timing with a stop watch. At the conclusion of the designated periods, the samples are placed in glass vials and labeled. Chewers are instructed to drink water between sessions to cleanse their palates. No eating or drinking is allowed during the chewing session. The samples are stored in a refrigerator/freezer. Nicotine content in residual gum is measured using a validated high performance liquid chromatography (HPLC) method. The percent dose (normalized to weight) of nicotine released at each time interval is determined by subtraction of residual nicotine remaining in the gum from the starting amount.

While the invention has been described with particular reference to smoking reduction or cessation, it is also within the scope hereof that the nicotine delivery system heretofore described also be utilized in the treatment of certain diseases as well. For example, studies have demonstrated that nicotine therapy can be particularly beneficial to persons with ulcerative colitis, Parkinson's disease, Tourette's syndrome and Alzheimer's disease as well.

EXAMPLES

The following examples are provided to elaborate upon the principals of the invention and are not intended to limit the scope of the invention. Tables 2, 4, and 6 set forth the compositions of various examples and comparative examples of medicated chewing gum compositions, with each of Tables 2, 4, and 6 reporting concentrations in percent by weight based on the total weight of the composition. Tables 3, 5, and 7 set forth the premix compositions for the examples and comparative examples of Tables 2, 4, and 6, respectively. Tables 3, 5, and 7 report premix concentrations based on parts by weight for the premix composition only. Tables 8-10 set forth the results of release measurement experiments for each of the examples and comparative examples, reporting the percent dose of nicotine released as a function of time (in minutes). These results are based on humans chewing the example gums at a chew rate of every 2 seconds. These results are reported as the mean % dose of nicotine release across three participants.

Example 1

4.40 mg of nicotine bitartrate dihydrate (NBD) was added to 70% sorbitol solution and stirred until the NBD partially dissolved into a white paste. The NDB solution was allowed to sit for several minutes. Sorbitol powder was added into a high speed food processor, then the NBD solution was added to form a premix. The premix was added to the gum formulation.

Example 2

Repeat procedures of Example 1, except at concentrations set forth for Example 2 in Table 2. The mixing of sorbitol solution and NBD solution was conducted for about 4 minutes, and the premix was screened before being added to the gum formulation.

Example 3

Repeat procedures of Example 1, except at concentrations set forth for Example 3 in Table 2.

Example 4

Repeat procedures of Example 1, except at concentrations set forth for Example 4 in Table 2. Water replaced sorbitol solution during preparation of the premix composition, and was evaporated off in an oven after premix was formed.

Example 5

Repeat procedures of Example 1, except at concentrations set forth for Example 5 in Table 2. Ethanol replaced the sorbitol solution during preparation of the premix composition, and was evaporated off after the premix was formed.

Example 6

Repeat procedures of Example 1, except at concentrations set forth for Example 6 in Table 2. Ethanol replaced the sorbitol solution during preparation of the premix composition.

Example 7

Repeat procedures of Example 5, except at concentrations set forth for Example 7 in Table 2. Ethanol was not evaporated off. Premix was screened before being added to the gum formulation.

Example 8

Repeat procedures of Example 5, except at concentrations set forth for Example 8 in Table 2. Ethanol was evaporated from the premix.

Example 9

Repeat procedures of Example 5, except at concentrations set forth for Example 9 in Table 2. Ethanol was not evaporated off.

Example 10

Repeat procedures of Example 5, except at concentrations set forth for Example 10 in Table 2. Ethanol was not evaporated off.

Example 11

Repeat procedures of Example 1, except at concentrations set forth for Example 11 in Table 4, and ethanol replaced the sorbitol solution during preparation of the premix composition.

Example 12

Repeat procedures of Example 1, except at concentrations set forth for Example 12 in Table 4.

Example 13

Repeat procedures of Example 1, except at concentrations set forth for Example 13 in Table 4. Ethanol replaced the sorbitol solution during preparation of the premix composition.

Example 14

Repeat procedures of Example 1, except at concentrations set forth in Table 4, and replace sorbitol solution with water as the solvent during preparation of the premix composition. Water was not evaporated from premix.

Example 15

Repeat procedures of Example 1, except at concentrations set forth in Table 4, and replace sorbitol solution with water as the solvent during preparation of the premix composition. Water was evaporated from premix, and the premix was screened prior to being added to the gum formulation.

Comparative Examples 16-26

Repeat procedures of Example 1, except at concentrations set forth for the comparative examples in Tables 4 and 6.

Comparative Example 27

No premix was added to the gum formulation, which included 0.67% NBD added directly to the sorbitol powder in the mixer.

TABLE 2

Gum compositions (pbw total composition; Examples 1-10)

| | Gum example # | | | | | | | | | |
|---|---|---|---|---|---|---|---|---|---|---|
| | 1 | 2 | 3 | 4 | 5 | 6 | 7 | 8 | 9 | 10 |
| Nicotine input (mg) | 4.40 | 2.20 | 2.20 | 2.20 | 2.20 | 2.20 | 2.20 | 2.20 | 2.20 | 2.20 |
| NTI gum base | 40.00 | 40.00 | 40.00 | 40.00 | 32.00 | 40.00 | 32.00 | 40.00 | 45.00 | 40.00 |
| Lycasin (85%) | | | | | 10.00 | | 10.00 | | | |
| Sorbitol 60W | 29.05 | 29.05 | 29.05 | 29.05 | 27.05 | 27.55 | 27.05 | 19.05 | 14.05 | 19.05 |
| Potassium carbonate | 4.50 | 4.50 | 4.50 | 4.50 | 4.50 | 6.00 | 4.50 | 4.50 | 4.50 | 4.50 |
| Sucralose | 0.10 | 0.10 | 0.10 | 0.10 | 0.10 | 0.10 | 0.10 | 0.10 | 0.10 | 0.10 |
| Acesulfame K | 0.20 | 0.20 | 0.20 | 0.20 | 0.20 | 0.20 | 0.20 | 0.20 | 0.20 | 0.20 |
| Menthol crystals | 0.65 | 0.65 | 0.65 | 0.65 | 0.65 | 0.65 | 0.65 | 0.65 | 0.65 | 0.65 |
| Super intense cooling mint flavor | 2.58 | 2.58 | 2.58 | 2.58 | 2.58 | 2.58 | 2.58 | 2.58 | 2.58 | 2.58 |
| Spearmint flavor | 0.72 | 0.72 | 0.72 | 0.72 | 0.72 | 0.72 | 0.72 | 0.72 | 0.72 | 0.72 |
| Spray dried peppermint powder | 2.20 | 2.20 | 2.20 | 2.20 | 2.20 | 2.20 | 2.20 | 2.20 | 2.20 | 2.20 |
| Premix | 20.00 | 20.00 | 20.00 | 20.00 | 20.00 | 20.00 | 20.00 | 30.00 | 30.00 | 30.00 |

TABLE 3

Premix compositions (pbw premix; Examples 1-10)

| | Gum example # | | | | | | | | | |
|---|---|---|---|---|---|---|---|---|---|---|
| | 1 | 2 | 3 | 4 | 5 | 6 | 7 | 8 | 9 | 10 |
| Sorbitol soltn (70%) | 15.00 | 10.00 | 5.00 | | | | | | | |
| Water | | | | 6.8 | | | | | | |
| Ethanol | | | | | 20.00 | 20.00 | 20.00 | 26.00 | 26.00 | 26.00 |
| Sorbitol powder | 78.06 | 86.62 | 91.62 | 96.62 | 76.62 | 76.62 | 76.62 | 97.75 | 97.75 | 97.75 |
| Mannitol | | | | | | | | | | |
| NBD | 6.69 | 3.38 | 3.38 | 3.38 | 3.38 | 3.38 | 3.38 | 2.25 | 2.25 | 2.25 |
| Yellow No. 10 | 0.25 | | | | | | | | | |

TABLE 4

Gum compositions (pbw total composition; Examples 11-16 and Comparative Examples 17-20)

| | Gum example # | | | | | | | | | |
|---|---|---|---|---|---|---|---|---|---|---|
| | 11 | 12 | 13 | 14 | 15 | 16 | 17 | 18 | 19 | 20 |
| Nicotine input (mg) | 2.20 | 2.20 | 2.20 | 2.20 | 2.20 | 2.20 | 2.20 | 2.20 | 2.20 | 2.20 |
| NTI gum base | 40.00 | 45.00 | 45.00 | 40.00 | 40.00 | 40.00 | 40.00 | 35.00 | 40.00 | |
| Magna T gum base | | | | | | | | | | 27.50 |
| Nova T gum base | | | | | | | | | | 27.50 |
| Lycasin (85%) | | | | | | | | 10.00 | | |
| Sorbitol 60W | 29.05 | 34.05 | 39.05 | 29.05 | 29.05 | 39.05 | 29.05 | 24.05 | 19.05 | 29.05 |
| Potassium carbonate | 4.50 | 4.50 | 4.50 | 4.50 | 4.50 | 4.50 | 4.50 | 4.50 | 4.50 | 4.50 |
| Sucralose | 0.10 | 0.10 | 0.10 | 0.10 | 0.10 | 0.10 | 0.10 | 0.10 | 0.10 | 0.10 |
| Acesulfame K | 0.20 | 0.20 | 0.20 | 0.20 | 0.20 | 0.20 | 0.20 | 0.20 | 0.20 | 0.20 |
| Menthol crystals | 0.65 | 0.65 | 0.65 | 0.65 | 0.65 | 0.65 | 0.65 | 0.65 | 0.65 | 0.65 |
| Super intense cooling mint flavor | 2.58 | 2.58 | 2.58 | 2.58 | 2.58 | 2.58 | 2.58 | 2.58 | 2.58 | 2.58 |
| Spearmint flavor | 0.72 | 0.72 | 0.72 | 0.72 | 0.72 | 0.72 | 0.72 | 0.72 | 0.72 | 0.72 |
| Spray dried peppermint powder | 2.20 | 2.20 | 2.20 | 2.20 | 2.20 | 2.20 | 2.20 | 2.20 | 2.20 | 2.20 |
| Premix | 20.00 | 10.00 | 5.00 | 20.00 | 20.00 | 10.00 | 20.00 | 20.00 | 30.00 | 5.00 |

TABLE 5

Premix compositions (pbw premix; Examples 11-16 and Comparative Examples 17-20)

| | Gum example # | | | | | | | | | |
|---|---|---|---|---|---|---|---|---|---|---|
| | 11 | 12 | 13 | 14 | 15 | 16 | 17 | 18 | 19 | 20 |
| Sorbitol soltn (70%) | | | | | | 10.00 | | | | |
| Water | | | | 6.80 | 6.8 | | | | | |
| Ethanol | 20.00 | 15.00 | 10.00 | | | | | | | |
| Sorbitol powder | 76.62 | 52.16 | 50.85 | 96.62 | 89.82 | | 91.62 | 96.62 | 97.75 | 57.52 |
| Mannitol | | 26.08 | 25.43 | | | 83.31 | | | | 28.76 |
| NBD | 3.38 | 6.76 | 13.72 | 3.38 | 3.38 | 6.69 | 3.38 | 3.38 | 2.25 | 13.72 |
| Lycasin (75%) | | | | | | | 5.00 | | | |

TABLE 6

Gum compositions (pbw total composition; Comparative Examples 21-27)

| | Gum example # | | | | | | |
|---|---|---|---|---|---|---|---|
| | 21 | 22 | 23 | 24 | 25 | 26 | 27 |
| Nicotine input (mg) | 2.20 | 2.20 | 2.20 | 2.20 | 2.20 | 2.20 | 2.20 |
| NTI gum base | | | 45.00 | 35.00 | 45.00 | 55.00 | 40.00 |
| Nova T gum base | 55.00 | | | | | | |
| Dreyco gum base | | 55.00 | | | | | |
| Sorbitol 60W | 29.05 | 29.05 | 34.05 | 48.48 | 37.55 | 29.05 | 46.38 |
| Potassium carbonate | 4.50 | 4.50 | 4.50 | 6.00 | 6.00 | 4.50 | 4.50 |
| NBD | | | | | | | 0.67 |
| Glycerin | | | 5.00 | | | | |
| Sucralose | 0.10 | 0.10 | 0.10 | 0.10 | 0.10 | 0.10 | 0.10 |
| Acesulfame K | 0.20 | 0.20 | 0.20 | 0.20 | 0.20 | 0.20 | 0.20 |
| Menthol crystals | 0.65 | 0.65 | 0.65 | 0.55 | 0.65 | 0.65 | 0.65 |
| Super intense cooling mint flavor | 2.58 | 2.58 | 2.58 | 2.19 | 2.58 | 2.58 | 2.58 |
| Spearmint flavor | 0.72 | 0.72 | 0.72 | 0.61 | 0.72 | 0.72 | 0.72 |
| Spray dried peppermint powder | 2.20 | 2.20 | 2.20 | 1.87 | 2.20 | 2.20 | 2.20 |
| Premix | 5.00 | 5.00 | 5.00 | 5.00 | 5.00 | 5.00 | 0.00 |

TABLE 7

Premix compositions (pbw premix; Comparative Examples 21-27)

| | Gum example # | | | | | | |
|---|---|---|---|---|---|---|---|
| | 21 | 22 | 23 | 24 | 25 | 26 | 27 |
| Sorbitol solution | | | | | | | N/A |
| Sorbitol powder | 57.52 | 57.52 | 57.52 | 57.69 | | 57.52 | N/A |
| Mannitol | 28.76 | 28.76 | 28.76 | 28.85 | | 28.72 | N/A |
| NBD | 13.72 | 13.72 | 13.72 | 13.46 | | 13.72 | N/A |

TABLE 8

Nicotine Release (percent dose) (ND = not determined)

| Time (min) | 1 | 2 | 3 | 4 | 5 | 6 | 7 | 8 | 9 | 10 |
|---|---|---|---|---|---|---|---|---|---|---|
| 1 | 38 | 35 | ND | ND | ND | ND | 23 | ND | ND | ND |
| 3 | 47 | 47 | 47 | ND | 39 | 42 | 34 | 40 | 37 | 40 |
| 5 | 52 | 53 | 58 | 54 | 50 | 48 | 43 | 45 | 45 | 47 |
| 10 | 64 | 66 | 74 | 72 | 65 | 64 | 59 | 59 | 60 | 58 |
| 20 | ND | ND | ND | ND | ND | ND | ND | ND | ND | ND |
| 30 | 84 | ND | ND | ND | ND | 83 | ND | ND | ND | ND |

TABLE 9

Nicotine Release (percent dose) (ND = not determined)

| Time (min) | 11 | 12 | 13 | 14 | 15 | 16 | 17 | 18 | 19 | 20 |
|---|---|---|---|---|---|---|---|---|---|---|
| 1 | ND | ND | ND | ND | 20 | 18 | ND | ND | ND | ND |
| 3 | 40 | 35 | 32 | 38 | 31 | 31 | 31 | 38 | 27 | 25 |
| 5 | 49 | 43 | 43 | 45 | 40 | 40 | 38 | 44 | 35 | 35 |
| 10 | 63 | 55 | 59 | 64 | 55 | 53 | 53 | 55 | 48 | 62 |
| 20 | ND | 73 | 74 | ND | ND | ND | ND | ND | ND | ND |
| 30 | 86 | 86 | 84 | ND | ND | 83 | ND | ND | ND | 89 |

TABLE 10

Nicotine Release (percent dose) (ND = not determined)

| Time (min) | 21 | 22 | 23 | 24 | 25 | 26 | 27 |
|---|---|---|---|---|---|---|---|
| 1 | ND | ND | ND | ND | ND | ND | 19 |
| 3 | 19 | 18 | 31 | 33 | 27 | 26 | 29 |
| 5 | 30 | 26 | 37 | 44 | 34 | 32 | 36 |
| 10 | 57 | 42 | 51 | 52 | 49 | 47 | 52 |
| 20 | ND | ND | ND | 66 | 59 | 66 | ND |
| 30 | 82 | 73 | 81 | ND | ND | 79 | 81 |

Figure 2:
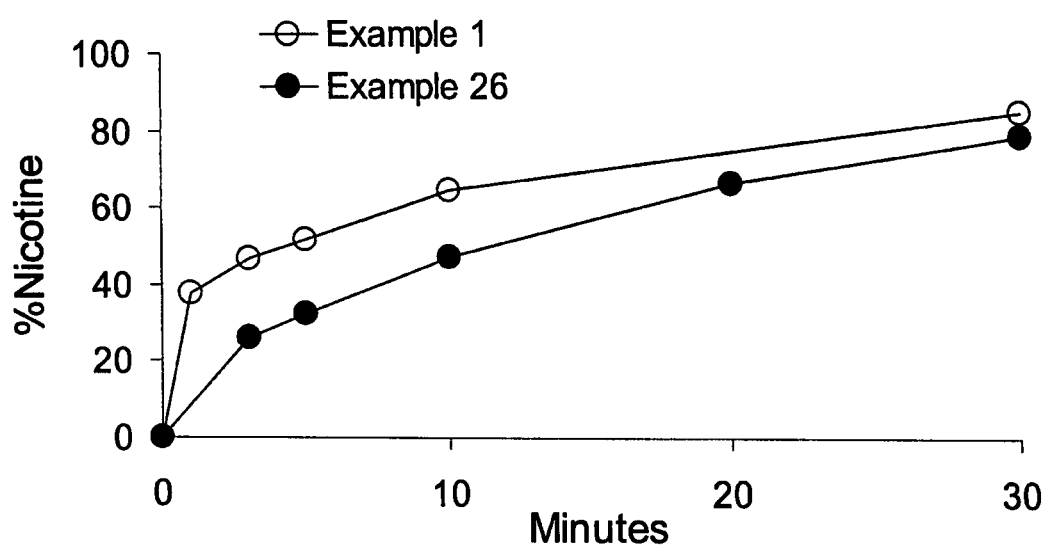
FIGS. 2 through 4 are graphs showing the nicotine release rates of several examples and comparative examples.

Each of Examples 1-3 containing sorbitol solution as a solvent exhibited an initial release rate of greater than 50 weight percent within 5 minutes of mastication followed by slower release over the remaining period of chewing. Example 4, which used a water solvent, had excellent release rate results but lesser uniformity of distribution than Examples 1-3, which utilized sorbitol solution as the solvent. FIG. 2 demonstrates in graphical format the differences between nicotine release rate between Example 1 (52 wt % release at 5 minutes) versus Comparative Example 26 (32 wt % release at 5 minutes), which did not include a solvent. By way of further comparison, but not illustrated in FIG. 2, Comparative Example 27 (no premix) had a release rate of 36 at 5 minutes.

Figure 3:
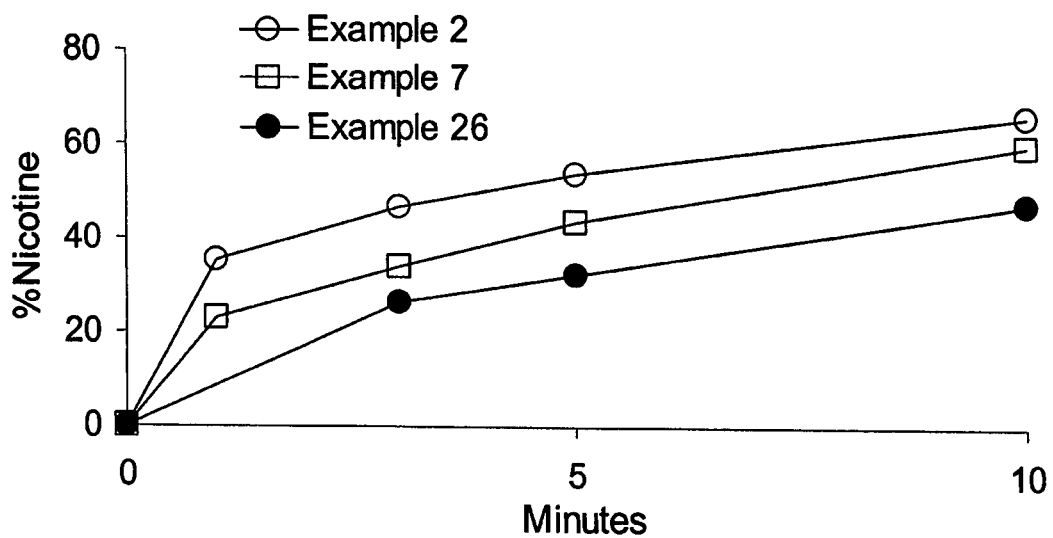

FIG. 3 illustrates in graphical format the release rates of Examples 2 and 7 and Comparative Example 26. Example 2 using a sorbitol solution solvent produced a release rate of 53 at 5 minutes. Example 7 had a less effective yet efficient release of 43 weight percent at 5 minutes. Each of these release rates was more than 10 weight percent greater than that of Comparative Example 26 over the same 5-minute time interval.

Figure 4:
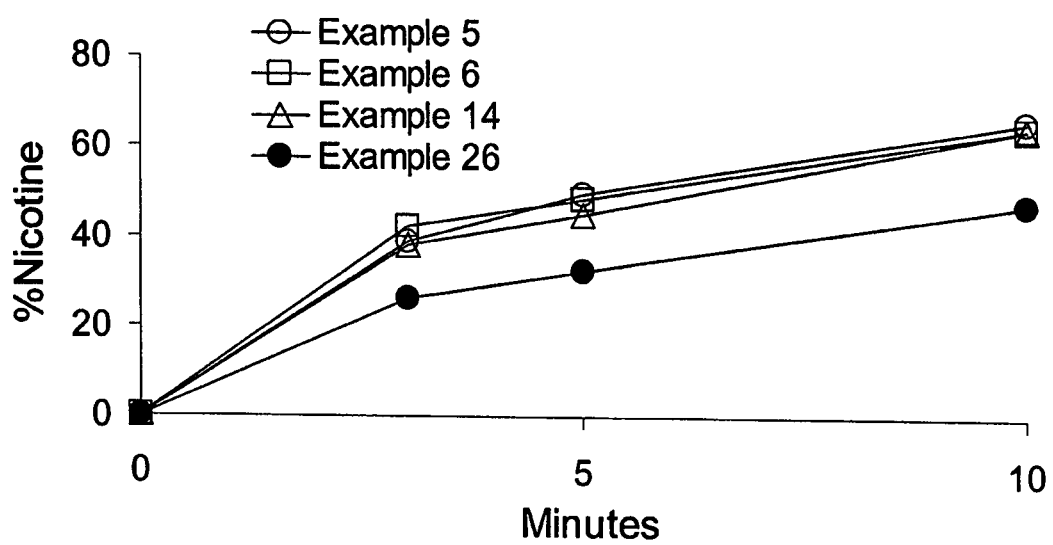

FIG. 4 illustrates a graph of the release rates of Examples 5, 6, and 14 and Comparative Example 26. The release rates of the examples were all at or above about 45 weight percent at 5 minutes, more than 10 weight percent greater than Comparative Example 26.

The following observations were also made. The inclusion of ethanol as a solvent in Examples 12 and 13 produced an improvement of about 8 wt % in release rate compared to similarly formulated Comparative Example 25, which did not contain ethanol or another solvent.

Examples 8-10, which were characterized by the partial dissolution of nicotine in ethanol to provide a white dispersion at room temperature, produced release rates that exhibited an improvement of 10 wt % or more at t=5 minutes compared to similarly formulated Comparative Example 19, which was free of solvent.

It is believed that Example 16, which included sorbitol solution, was not as effective as other examples because the premix contained mannitol, which did not hydrate as fast as sorbitol would in the gum during chewing. Similarly, it is believed that the reduced release rates of Examples 12 and 13 (43 each) was attributable to the presence of the less soluble mannitol in the premix.

Examples 28 and 29

Additional exemplary chewing gum compositions are set forth in Table 11 below, and premix compositions are set forth in Table 12 below. For each of examples 28 and 29, sorbitol powder and yellow color were mixed in a food processor (or other high speed mixer) at low setting for 1 minute at concentrations set forth for the comparative examples in Tables 11 and 12. In a stainless steel container, NBD was added to sorbitol solution (70%) and mixed by hand with a spatula for 1 minute. The nicotine/sorbitol solution mixture was slowly added to the sorbitol/color mix in the food processor and mixed for 4 minutes at low setting. The resulting premix composition was screened through a 10 mesh (2000 microns) stainless steel screen. The premix was added to the gum formulation.

TABLE 11

Gum compositions (pbw total composition; Examples 28 & 29)

| | Gum example # | |
|---|---|---|
| | 28 | 29 |
| Nicotine input (mg): | 4.00 | 4.00 |
| Gum Base: | | |
| Butyl rubber | 2.600 | 3.575 |
| BHT | 0.024 | 0.033 |
| Ester 5 | 4.160 | 5.720 |
| Soybean Oil, Partially Hydrogenated | 7.236 | 9.950 |
| Polyisobutylene | 3.600 | 4.950 |
| Dicalcium Phosphate, Anhydrous, USP (Powder) | 8.180 | 11.247 |
| Polyvinyl Acetate | 9.600 | 13.200 |
| Wax, Microcrystalline | 2.000 | 2.750 |
| Mono And Diglycerides | 2.600 | 3.575 |
| Excipients, Buffer, Active: | | |
| Sorbitol 60W | 29.050 | 29.050 |
| Acesulfame K | 0.200 | 0.200 |
| Sucralose, Micronized | 0.100 | 0.100 |
| Potassium Carbonate, Extra Fine Anhydrous | 4.500 | 4.500 |
| Flavor System: | | |
| Cooling mint flavor | 2.580 | 2.580 |
| Menthol Crystals | 0.650 | 0.650 |
| Peppermint Flavor, Spray Dried | 2.200 | 2.200 |
| Spearmint Oil | 0.720 | 0.720 |
| Premix | 20.000 | 5.000 |

TABLE 12

Premix compositions (pbw premix; Examples 28 and 29)

| | Gum example # | |
|---|---|---|
| | 28 | 29 |
| Sorbitol solutn (70%) | 3.000 | |
| NBD | 1.356 | 1.359 |
| Sorbitol powder | 15.594 | 2.394 |
| Mannitol powder | | 1.197 |
| Yellow No. 10 | 0.050 | 0.050 |

Processing aids used during mixing of gum examples 28 and 29 included talc and sterile water.

Examples 28, 29, and NICORETTE® FreshMint (4 mg) were evaluated in a single dose, randomized, crossover bioavailability pilot study. The study's primary objective was to compare the plasma nicotine absorption of a single 4 mg dose of Example 28 relative to a single 4 mg dose of Example 29 and a single 4 mg dose of NICORETTE gum within the first 10 minutes of dosing (i.e., $AUC_{0-10}$) in healthy adult smokers. The test group consisted of 14 individuals between the ages of 20 and 40, 64% male and 36% female, median age 26. The test group averaged 10 cigarettes per day (11.6±6.2), and 5.5 years as the median number of years smoked (9.1±7.9). Nicotine plasma concentration levels were then tested at specified time intervals. Baseline-adjusted plasma levels at each time interval was calculated using the following formula:

$C_T(adj) = C_T - [C_{-5} - C_{-5}e^{-Kt}]$, wherein $K = 0.693/t_{1/2}$, t=timepoint, and $t_{1/2}$=nicotine half-life. Mean plasma concentration data for raw data and adjusted baseline data are provided in Table 13 below:

TABLE 13

(Mean nicotine plasma concentration data for examples 28, 29 & NICORETTE)

| | | RAW | | | BASELINE ADJUSTED | | |
|---|---|---|---|---|---|---|---|
| Example # | Time (minutes) | N | Mean | Std Dev | N | Mean | Std Dev |
| 28 | 0 | 14 | 4.76 | 2.64 | 14 | 0.00 | 0.00 |
| | 2 | 14 | 5.34 | 2.80 | 13 | 0.66 | 1.09 |
| | 4 | 14 | 7.57 | 4.45 | 13 | 2.74 | 4.24 |
| | 6 | 13 | 8.62 | 4.69 | 13 | 3.89 | 3.98 |
| | 8 | 13 | 10.24 | 4.63 | 13 | 5.56 | 4.47 |
| | 10 | 13 | 11.40 | 4.34 | 13 | 6.78 | 4.33 |
| | 15 | 14 | 13.58 | 4.37 | 13 | 9.15 | 4.05 |
| | 30 | 14 | 15.63 | 4.85 | 13 | 11.76 | 4.28 |
| | 45 | 14 | 17.75 | 7.10 | 13 | 14.27 | 6.17 |
| | 60 | 14 | 17.75 | 7.28 | 13 | 14.57 | 6.22 |
| | 90 | 14 | 16.66 | 7.12 | 13 | 13.83 | 6.39 |
| | 180 | 14 | 11.99 | 6.36 | 13 | 10.36 | 6.03 |
| 29 | 0 | 14 | 4.72 | 3.42 | 14 | 0.00 | 0.00 |
| | 2 | 14 | 4.77 | 3.27 | 14 | 0.48 | 0.83 |
| | 4 | 13 | 5.15 | 2.85 | 14 | 0.76 | 0.92 |
| | 6 | 13 | 6.27 | 2.73 | 14 | 1.73 | 1.78 |
| | 8 | 14 | 7.66 | 3.17 | 14 | 3.40 | 2.84 |
| | 10 | 14 | 8.21 | 3.57 | 14 | 3.96 | 3.78 |
| | 15 | 14 | 10.75 | 4.22 | 14 | 6.54 | 4.54 |
| | 30 | 14 | 13.56 | 3.96 | 14 | 9.70 | 4.62 |
| | 45 | 14 | 14.68 | 5.22 | 14 | 11.14 | 4.59 |
| | 60 | 14 | 15.11 | 5.87 | 14 | 11.87 | 4.94 |
| | 90 | 14 | 13.07 | 5.64 | 14 | 10.34 | 4.71 |
| | 180 | 14 | 9.15 | 4.01 | 14 | 7.53 | 3.41 |
| NICORETTE FreshMint | 0 | 13 | 4.92 | 4.42 | 13 | 0.00 | 0.00 |
| | 2 | 14 | 5.50 | 4.68 | 13 | 0.32 | 0.43 |
| | 4 | 14 | 5.31 | 4.56 | 13 | 0.21 | 0.26 |
| | 6 | 13 | 5.59 | 4.53 | 13 | 0.50 | 0.51 |
| | 8 | 14 | 6.12 | 4.38 | 13 | 1.10 | 1.10 |
| | 10 | 14 | 6.94 | 4.67 | 13 | 1.93 | 1.77 |
| | 15 | 14 | 9.04 | 5.35 | 13 | 3.86 | 2.03 |
| | 30 | 14 | 13.55 | 5.49 | 13 | 8.64 | 3.57 |
| | 45 | 14 | 15.87 | 6.25 | 13 | 11.03 | 2.88 |
| | 60 | 14 | 16.57 | 8.20 | 13 | 11.40 | 2.57 |
| | 90 | 14 | 14.61 | 7.41 | 13 | 10.31 | 2.98 |
| | 180 | 14 | 10.42 | 6.19 | 13 | 7.60 | 3.37 |

Figure 5:
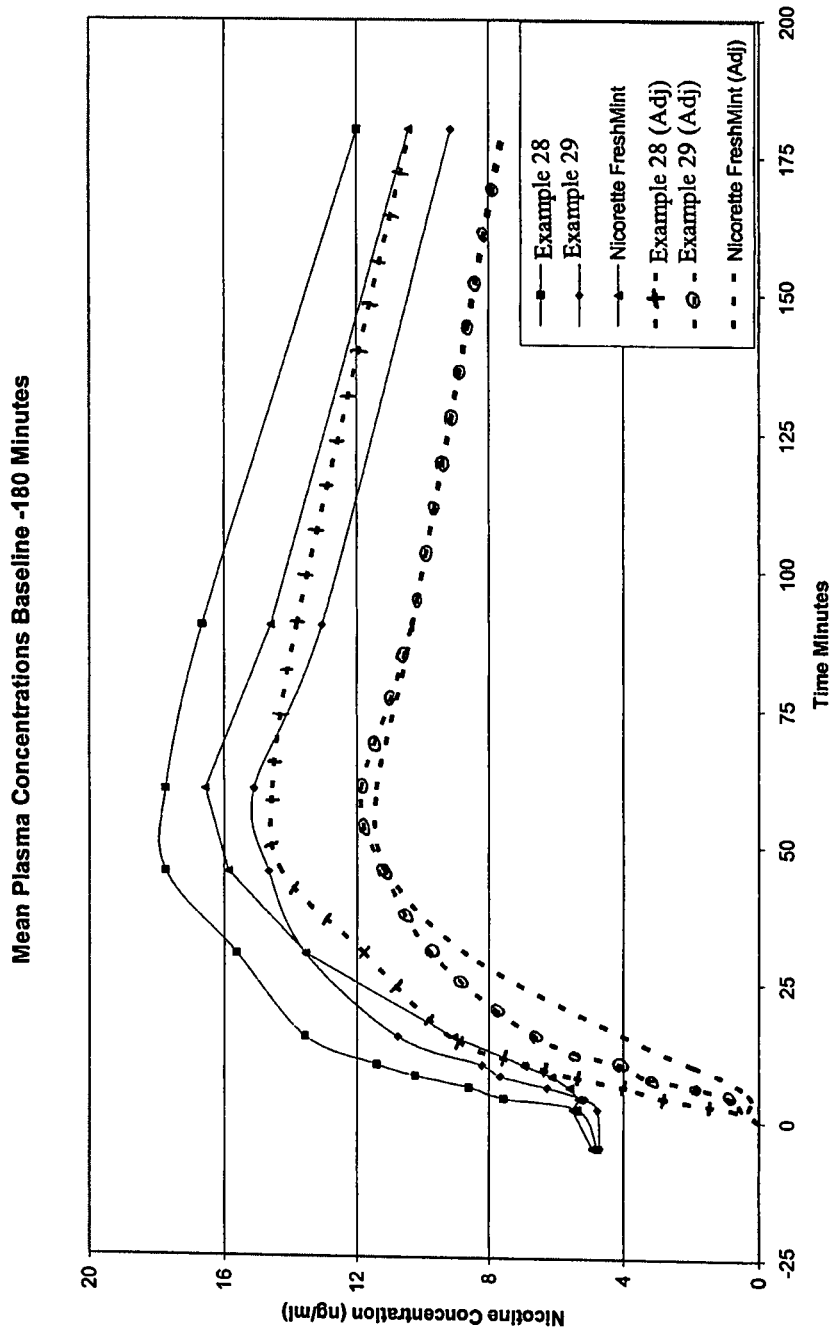
FIGS. 5 and 6 are graphs showing mean plasma nicotine concentration plots of several examples and for NICORETTE FreshMint (4 mg) chewing gum, with baseline adjusted levels shown in dashed lines.
Figure 6:
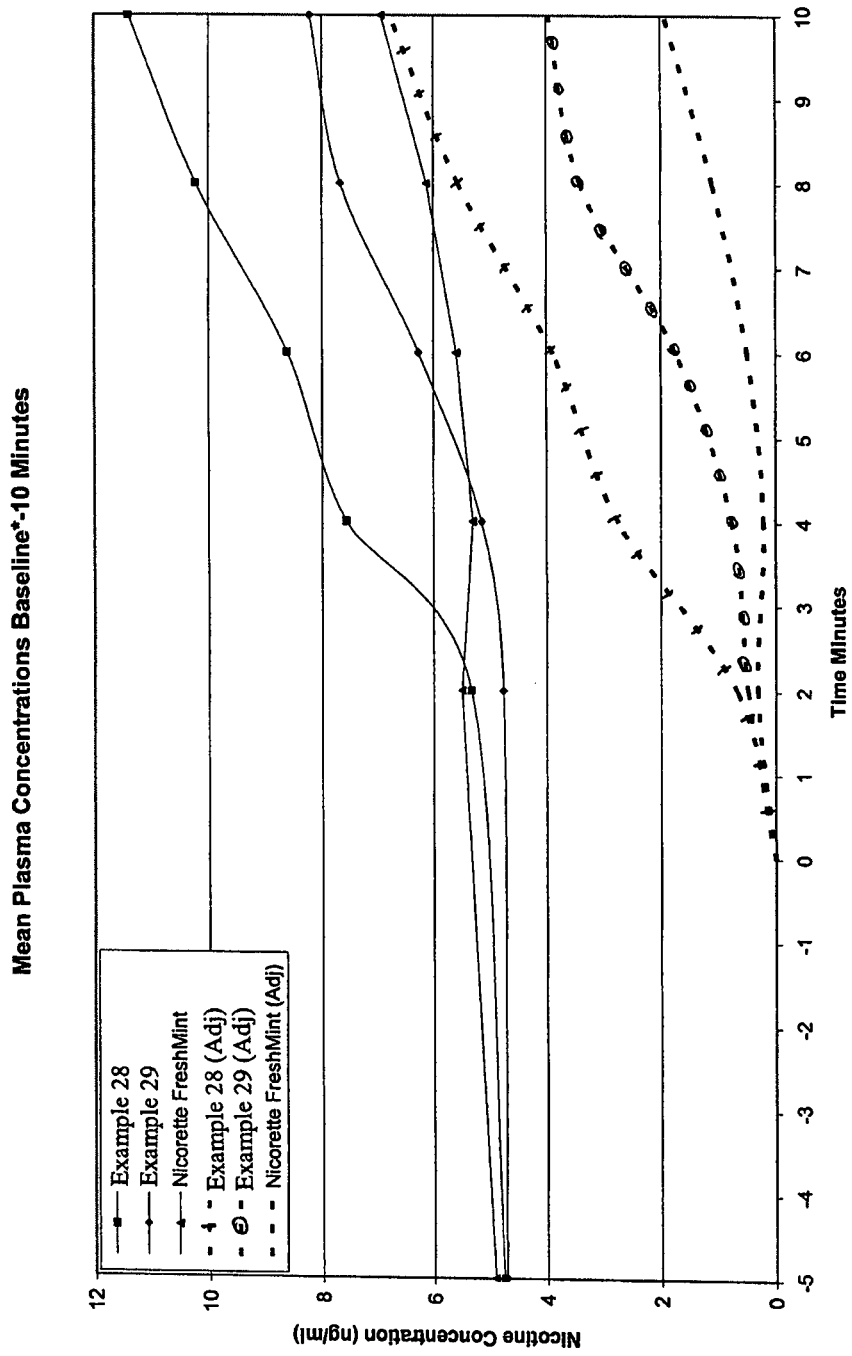

FIG. 5 demonstrates in graphical format the mean plasma concentrations of examples 28, 29 and NICORETTE in ng/mL, based on data from time intervals of 0, 2, 4, 6, 8, 10, 15, 30, 45, 60, 90 and 180 minutes. Raw data baseline is −5 minutes; adjusted data baseline is 0 minutes. From time −5 minutes to 10 minutes is also shown in graphical format in FIG. 6. At 4 minutes, example #28 achieved a nicotine plasma concentration substantially higher than either example #29 or the comparative NICORETTE example.

Mean pharmacokinetic parameter estimates for raw plasma concentration data and for baseline adjusted plasma concentration data were calculated using area under the curve (AUC) calculations, such as disclosed by Rowland M, Tozer T N, *Clinical Pharmacokinetics: Concepts and Applications*, Lea & Febiger, Philadelphia, p. 21 (1989), the disclosure of which is incorporated herein by reference. Pharmacokinetic parameter estimates based on raw data are provided in Table 14 below. Pharmacokinetic parameter estimates based on baseline adjusted data are provided in Table 15 below. As can be seen in Tables 14 and 15, the mean $AUC_{0-10}$ for Example 28 was significantly greater than the NICORETTE example. These results indicate that plasma nicotine levels were significantly greater for Example 28 than NICORETTE during the first 10 minutes of chewing. Similarly, Example 28 delivered significantly more nicotine compared to Example 29 and the NICORETTE example during the first 90 minutes of plasma sampling and during the entire 180 minutes of plasma sampling.

TABLE 14

(Parameter Estimates from raw data for examples 28, 29 & NICORETTE in ng/mL*minutes)
Mean (±S.D.) Pharmacokinetic Parameter Estimates - Raw Plasma Concentrations

| Measure | Example 28 | Example 29 | NICORETTE FreshMint | Example 28 v. Example 29 (p values) | Example 28 v. NICORETTE (p values) | Example 29 v. NICORETTE (p values) |
|---|---|---|---|---|---|---|
| $AUC_{0-10}$ (trapezoidal) | 79.69 ± 36.54 | 59.93 ± 27.25 | 52.20 ± 42.56 | 0.0857 | 0.0342 | 0.6167 |
| $AUC_{0-10}$ (log transformed) | 72.32 ± 1.60 | 53.98 ± 1.64 | 40.58 ± 2.07 | 0.0895 | 0.0036 | 0.1372 |
| $AUC_{0-90}$ (trapezoidal) | 1410.06 ± 522.87 | 1147.56 ± 388.72 | 1090.93 ± 403.85 | 0.0079 | 0.0110 | 0.9478 |
| $AUC_{0-90}$ (log transformed) | 1323.09 ± 1.46 | 1089.97 ± 1.39 | 1036.9 ± 1.37 | 0.0125 | 0.0106 | 0.8822 |
| $AUC_{0-180}$ (trapezoidal) | 2707.72 ± 1141.58 | 2147.33 ± 804.37 | 2100.79 ± 832.93 | 0.0021 | 0.0113 | 0.5411 |
| $AUC_{0-180}$ (log transformed) | 2502.00 ± 1.51 | 2023.48 ± 1.42 | 1981.84 ± 1.40 | 0.0030 | 0.0097 | 0.6820 |
| $C_{max}$ | 19.62 ± 7.29 | 16.07 ± 5.75 | 15.75 ± 4.81 | 0.0085 | 0.0250 | 0.6859 |
| $T_{max}$ | 53.08 ± 15.75 | 47.14 ± 19.39 | 55.38 ± 15.47 | 0.4653 | 0.7226 | 0.2801 |

TABLE 15

(Parameter Estimates from baseline adjusted data for examples 28, 29 & NICORETTE in ng/mL*minutes)
Mean (±S.D.) Pharmacokinetic Parameter Estimates - Baseline Adjusted Plasma Concentrations

| Measure | Example 28 | Example 29 | NICORETTE FreshMint | Example 28 v. Example 29 (p values) | Example 28 v. NICORETTE (p values) | Example 29 v. NICORETTE (p values) |
|---|---|---|---|---|---|---|
| $AUC_{0-10}$ (trapezoidal) | 32.49 ± 30.24 | 16.70 ± 13.96 | 6.17 ± 5.07 | 0.0262 | 0.0011 | 0.1716 |
| $AUC_{0-10}$ (log transformed) | 23.29 ± 2.32 | 11.03 ± 2.95 | 4.23 ± 2.65 | 0.0533 | 0.0001 | 0.0161 |
| $AUC_{0-90}$ (trapezoidal) | 1066.60 ± 417.39 | 826.98 ± 329.17 | 755.77 ± 183.20 | 0.0079 | 0.0054 | 0.8103 |
| $AUC_{0-90}$ (log transformed) | 998.65 ± 1.46 | 769.58 ± 1.48 | 734.64 ± 1.29 | 0.0180 | 0.0157 | 0.9028 |
| $AUC_{0-180}$ (trapezoidal) | 2155.43 ± 958.92 | 1631.12 ± 657.32 | 1561.86 ± 419.30 | 0.0007 | 0.0029 | 0.6277 |
| $AUC_{0-180}$ (log transformed) | 1988.06 ± 1.51 | 1525.79 ± 1.45 | 1512.00 ± 1.30 | 0.0018 | 0.0081 | 0.5870 |
| $C_{max}$ | 16.03 ± 6.20 | 12.77 ± 5.17 | 12.37 ± 2.72 | 0.0116 | 0.0231 | 0.8124 |
| $T_{max}$ | 53.08 ± 15.75 | 50.36 ± 17.26 | 58.85 ± 16.73 | 0.7058 | 0.4020 | 0.2240 |

While this invention has been described as having a preferred design, it is understood that it is capable of further modifications, uses and/or adaptations of the invention, following in general the principle of the invention and including such departures from the present disclosure as come within known or customary practice in the art to which the invention pertains, and as may be applied to the central features hereinbefore set forth, and fall within the scope of the invention of the limits of the appended claims.

What is claimed is:

1. A method of making a medicinal delivery system for oral delivery of a nicotine compound which satiates nicotine craving for an individual in need of nicotine-craving relief, comprising:
providing a paste comprising a solvent-treated nicotine compound that has been at least partially dissolved in a solvent of a bulk sweetener solution to make the nicotine compound more readily dissolvable during ingestion or mastication to promote a high initial nicotine release rate;
coating a saliva-soluble bulk sweetener powder with the paste to establish a coated powder premix; and
subsequent to establishing the coated powder premix, distributing the coated powder premix in an edible carrier base selected from the group consisting of a chewing gum base and a lozenge base and combining the edible carrier base and the coated powder premix with a buffer to establish a medicinal delivery system,
wherein the nicotine compound comprises at least one member selected from the group consisting of nicotine, nor-nicotine, lobeline, free base nicotine, and pharmacologically acceptable salts of nicotine.

2. The method of claim 1, wherein the bulk sweetener solution comprises a sorbitol solution.

3. The method of claim 1, wherein the saliva-soluble bulk sweetener powder comprises a bulk sweetener selected from the group consisting of sorbitol, xylitol, mannitol, isomalt, maltitol, and lactitol.

4. The method of claim 1, wherein the saliva-soluble bulk sweetener powder comprises sorbitol powder.

5. The method of claim 1, wherein the solvent of the bulk sweetener solution has been removed from the paste prior to said coating of the saliva-soluble bulk sweetener powder.

6. The method of claim 1, wherein the solvent of the bulk sweetener solution is retained in the paste for said coating of the saliva-soluble bulk sweetener powder.

7. The method of claim 1, wherein the carrier base comprises chewing gum.

8. The method of claim 1, wherein the carrier base comprises a lozenge.

9. The method of claim 1, wherein the medicinal delivery system provides for about 45% or more release of the nicotine compound within 5 minutes of the onset of ingestion or mastication.

10. The method of claim 1, wherein the medicinal delivery system provides for about 50% or more release of the nicotine compound within 5 minutes of the onset of ingestion or mastication.

11. A method of making a medicinal delivery system for oral delivery of a nicotine compound which satiates nicotine craving for an individual in need of nicotine-craving relief, comprising:

at least partially dissolving a nicotine compound in a solvent of a bulk sweetener solution to form a paste;

coating a saliva-soluble bulk sweetener powder with the paste to establish a coated powder premix; and subsequent to establishing the coated powder premix, distributing the coated powder premix in an edible carrier base selected from the group consisting of a chewing gum base and a lozenge base and combining the edible carrier base and the coated powder premix with a buffer to establish a medicinal delivery system, wherein the nicotine compound comprises at least one member selected from the group consisting of nicotine, nor-nicotine, lobeline, free base nicotine, and pharmacologically acceptable salts of nicotine.

12. The method of claim 11, wherein the bulk sweetener solution comprises a sorbitol solution.

13. The method of claim 11, wherein the saliva-soluble bulk sweetener powder comprises a bulk sweetener selected from the group consisting of sorbitol, xylitol, mannitol, isomalt, maltitol, and lactitol.

14. The method of claim 11, wherein the saliva-soluble bulk sweetener powder comprises sorbitol powder.

15. The method of claim 11, further comprising removing the solvent of the bulk sweetener solution from the paste prior to said coating of the saliva-soluble bulk sweetener powder.

16. The method of claim 11, further comprising retaining the solvent of the bulk sweetener solution in the paste for said coating of the saliva-soluble bulk sweetener powder.

17. The method of claim 11, wherein the carrier base comprises chewing gum.

18. The method of claim 11, wherein the carrier base comprises a lozenge.

19. The method of claim 11, wherein the medicinal delivery system provides for about 45% or more release of the nicotine compound within 5 minutes of the onset of ingestion or mastication.

20. The method of claim 11, wherein the medicinal delivery system provides for about 50% or more release of the nicotine compound within 5 minutes of the onset of ingestion or mastication.

* * * * *